(12) United States Patent
Hirata et al.

(10) Patent No.: US 8,405,903 B2
(45) Date of Patent: Mar. 26, 2013

(54) OBJECTIVE-OPTICAL-SYSTEM POSITIONING APPARATUS AND EXAMINATION APPARATUS

(75) Inventors: Tadashi Hirata, Tokyo (JP); Masahiro Oba, Tokyo (JP)

(73) Assignee: Olympus Corporation, Tokyo (JP)

( * ) Notice: Subject to any disclaimer, the term of this patent is extended or adjusted under 35 U.S.C. 154(b) by 325 days.

(21) Appl. No.: 12/790,112

(22) Filed: May 28, 2010

(65) Prior Publication Data

US 2010/0309547 A1   Dec. 9, 2010

(30) Foreign Application Priority Data

Jun. 2, 2009   (JP) ................................. 2009-133449

(51) Int. Cl.
*G02B 21/00* (2006.01)
*G02B 21/02* (2006.01)

(52) U.S. Cl. ......................... 359/368; 359/656; 359/819

(58) Field of Classification Search .................. 359/368, 359/382, 384, 390, 656, 819–830
See application file for complete search history.

(56) References Cited

U.S. PATENT DOCUMENTS

| | | | | |
|---|---|---|---|---|
| 5,295,477 A | * | 3/1994 | Janfaza | 600/142 |
| 5,496,261 A | * | 3/1996 | Sander | 600/163 |
| 5,588,949 A | * | 12/1996 | Taylor et al. | 600/166 |
| 7,304,789 B2 | * | 12/2007 | Hirata et al. | 359/368 |
| 2007/0097494 A1 | * | 5/2007 | Tokuda et al. | 359/368 |

FOREIGN PATENT DOCUMENTS

| | | |
|---|---|---|
| JP | 2006-119300 A | 5/2005 |
| JP | 2005-241671 A | 9/2005 |
| JP | 2005-253836 A | 9/2005 |

\* cited by examiner

*Primary Examiner* — Thong Nguyen
(74) *Attorney, Agent, or Firm* — Holtz, Holtz, Goodman & Chick, P.C.

(57) ABSTRACT

An objective-optical-system positioning apparatus includes a positioning unit interposed between an objective optical system having a small-diameter end section and an examination optical system for examining light collected by the objective optical system; and a substantially cylindrical support unit, one end of which is secured to an organism, and which internally supports the small-diameter end section in a detachable manner. The positioning unit includes a holding part for holding the objective optical system and a moving mechanism supporting the holding part such that the holding part is freely movable in a direction intersecting with a direction of an optical axis of the objective optical system, and the other end of the support unit has a tapered inner surface whose diameter gradually increases toward the tip.

8 Claims, 7 Drawing Sheets

OBJECTIVE-OPTICAL-SYSTEM POSITIONING APPARATUS AND EXAMINATION APPARATUS

BACKGROUND OF THE INVENTION

1. Field of the Invention

The present invention relates to an objective-optical-system positioning apparatus and an examination apparatus.

This application is based on Japanese Patent Application No. 2009-133449, the content of which is incorporated herein by reference.

2. Description of Related Art

Recently, it has become important to examine the condition of the inside, e.g., deep portions of the brain or organs, of biological specimens, such as small animals, while they are still alive (in vivo). Therefore, there is a known objective optical system and microscope system having a small-diameter end section, which enables in vivo time-sequential examination for a relatively long period of time by reducing the level of invasiveness on an organism (for example, Japanese Unexamined Patent Applications, Publication Nos. 2006-119300 and 2005-241671).

When performing in vivo examination in the passage of time, to allow activity of the small animal, etc., which is similar to that during normal times, it is necessary to temporarily remove the objective optical system positioned at an examination site and then position the objective optical system at the same examination site again for examination. There is a known securing device that positions the objective optical system at this time with high reproducibility by inserting the objective optical system into en insertion hole of a support member secured to an organism (for example, Japanese Unexamined Patent Application, Publication No. 2005-253836).

When the inside of an organism is to be examined with a low level of invasiveness on the organism and for a relatively long period of time by using both an objective optical system having a small-diameter end section and a securing device, it is desirable to keep the inner diameter of the insertion hole to a size slightly larger than the outer diameter of the small-diameter end section to decrease the level of invasiveness of the support member on the organism.

Therefore, when the diameter of the insertion hole is decreased, the gap between the small-diameter end section and the insertion hole becomes very small when the small-diameter end section removed from the insertion hole is inserted again into the insertion hole.

BRIEF SUMMARY OF THE INVENTION

The present invention has been conceived in light of the above-described circumstances, and it is an object thereof to provide an objective-optical-system positioning apparatus and an examination apparatus that enable a small-diameter end section of an objective optical system to be easily inserted into an insertion hole while preventing damage to the objective optical system and/or the support member, as well as any adverse effect on an organism, even when the insertion hole of the support member has a small diameter.

To achieve the above-described object, the present invention provides the following solution.

The present invention provides an objective-optical-system positioning apparatus including a positioning unit interposed between an objective optical system having a small-diameter end section and an examination optical system configured to examine light collected by the objective optical system; and a substantially cylindrical support unit, one end of which is secured to an organism, and which internally supports the small-diameter end section in a detachable manner, wherein the positioning unit includes a holding part for holding the objective optical system and a moving mechanism supporting the holding part such that the holding part is freely movable in a direction intersecting the direction of an optical axis of the objective optical system, and wherein the other end of the support unit has a tapered inner surface whose diameter gradually increases toward a tip thereof.

DETAILED DESCRIPTION OF THE INVENTION

An objective-optical-system positioning apparatus 1 and an examination apparatus 100 according to an embodiment of the present invention will be described below with reference to FIGS. 1 to 10. In this embodiment, an example in which the inside of the brain of a live mouse (organism) A is examined will be described.

Figure 1:
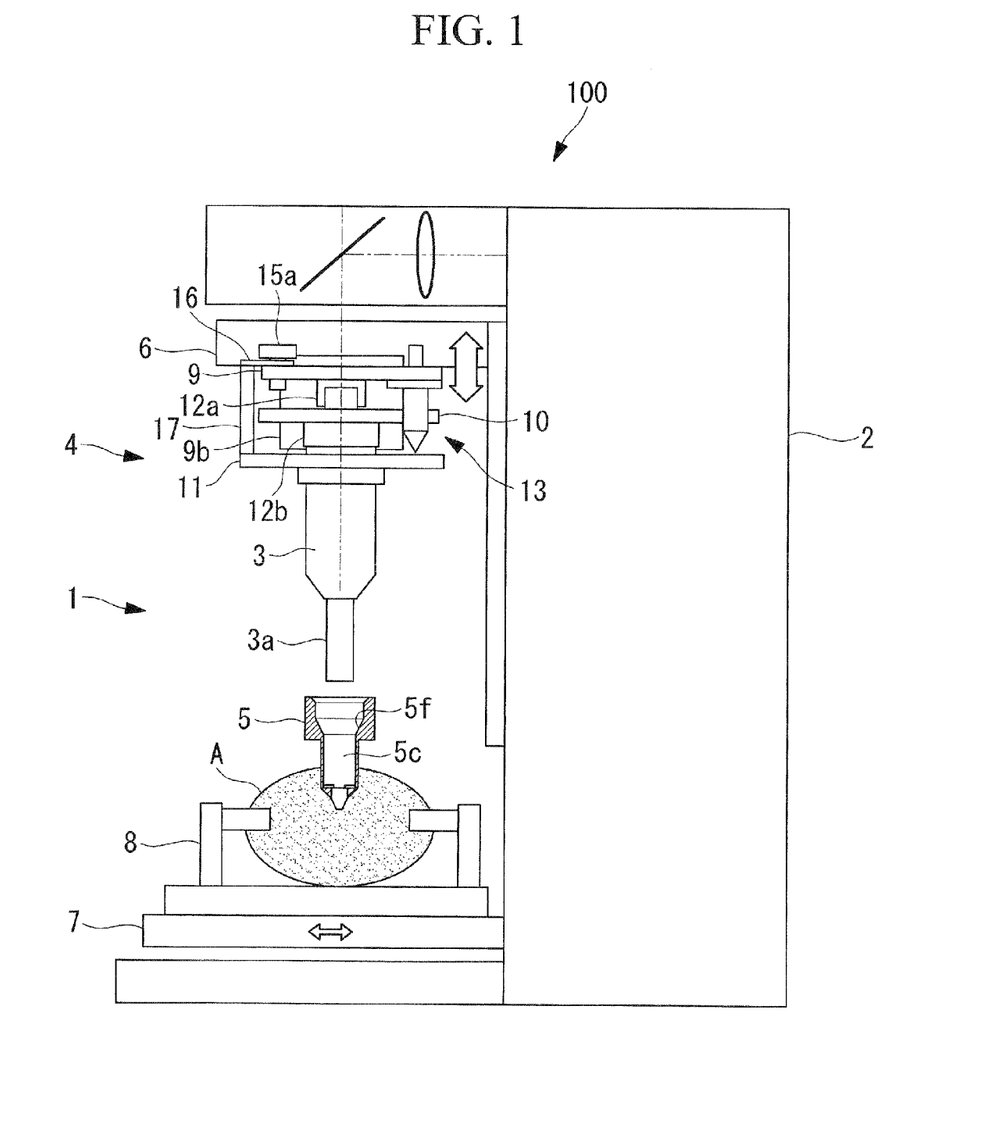
FIG. 1 is an overall configuration diagram of an objective-optical-system positioning apparatus and an examination apparatus according to an embodiment of the present invention.

As illustrated in FIG. 1, the base of the examination apparatus 100 according to this embodiment is an upright optical microscope. The examination apparatus 100 includes a microscope (examination optical system) 2 and the objective-optical-system positioning apparatus 1 according to this embodiment having a positioning unit 4, which is mounted on the microscope 2 and to which an objective optical system 3 is attached, and a support unit 5, which is secured to the mouse A.

As the microscope 2, a typical optical microscope or a laser scanning microscope is used. The microscope 2 has a unit attachment part 6 to which the positioning unit 4 is attached. The unit attachment part 6 has a structure typically used for mounting an objective optical system, and, for example, is provided with an RMS screw. By moving the unit attachment part 6 up and down along the direction of the optical axis, the positions of the positioning unit 4 and the objective optical system 3, which is attached to the unit attachment part 6, are adjusted in the height direction. The mouse A is placed on a stage 7, which is movable on a horizontal plane, and the head region is secured to the stage 7 with a securing member 8.

The objective optical system 3 has a small-diameter end section 3a. The objective optical system 3 has an infinity design in which light collected from the tip of the objective optical system 3 is transmitted to subsequent optical systems as a substantially parallel beam of light.

Figure 2:
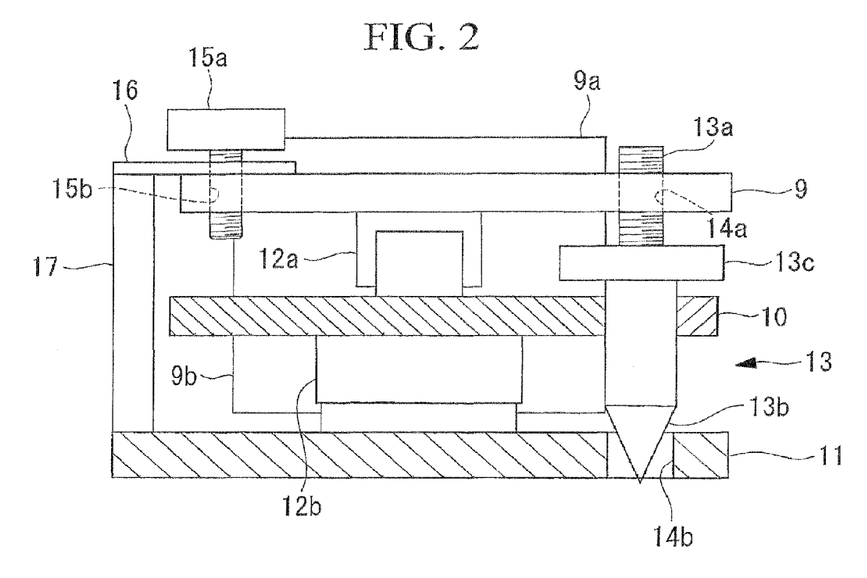
FIG. 2 is an overall configuration diagram illustrating a positioning unit of the objective-optical-system positioning apparatus in FIG. 1.

As illustrated in FIG. 2, the positioning unit 4 is provided with a microscope attachment part 9, an intermediate part 10, and an, objective attachment part (holding part) 11, in this order from the microscope 2. An X-axis guide 12a (moving mechanism, linear guide) is interposed between the microscope attachment part 9 and the intermediate part 10. A Y-axis guide 12b (moving mechanism, linear guide) is interposed between the intermediate part 10 and the objective attachment part 11. The X-axis guide 12a and the Y-axis guide 12b are movable in directions orthogonal to each other on a plans orthogonal to the optical axis of the microscope 2. As the guides 12a and 12b, structures that have excellent slideability, for example, a structure having bearings (bearing mechanisms), are used. In this way, the objective attachment part 11 is movably supported with respect to the microscope attachment part 9 on the horizontal plane.

Figure 3:
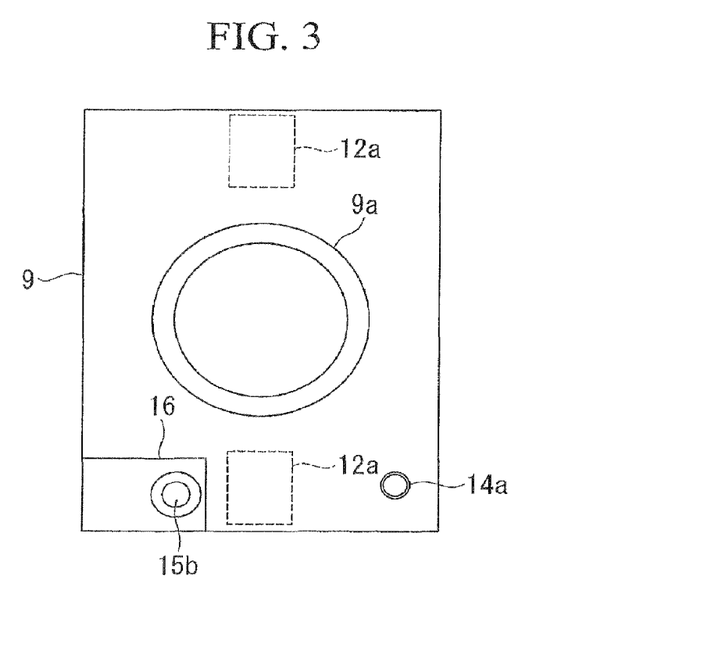
FIG. 3 is a front view of a microscope attachment part of the positioning unit in FIG. 2.

As illustrated in FIG. 3, the microscope attachment part 9 has a microscope attachment screw 9a that is removable from the unit attachment part 6 of the microscope 2. By attaching the microscope attachment screw 9a to the unit attachment part 6, the positioning unit 4 is mounted on the microscope 2. A light-blocking cylinder 9b, which extends near the objective attachment part 11, is provided at substantially the center of the microscope attachment part 9. In this way, light is blocked from entering from outside into the light path between the microscope 2 and the objective optical system 3, and stray light is prevented from being mixed into the illumination light from the microscope 2 and the examination light collected by the objective optical system 3.

Figure 4:
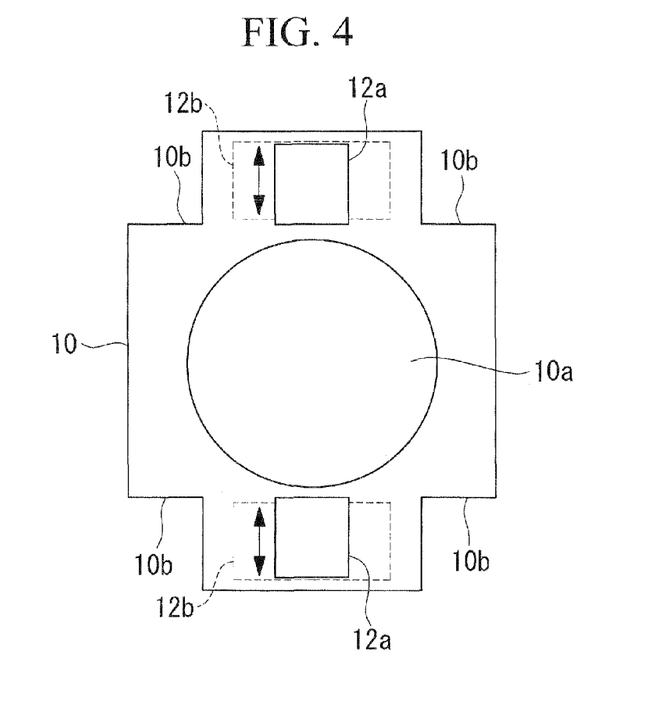
FIG. 4 is a front view of an intermediate part of the positioning unit in FIG. 2.

As illustrated in FIG. 4, an intermediate-part hole 10a through which the light-blocking cylinder 9b penetrates is formed at substantially the center of the intermediate part 10. The intermediate-part hole 10a has an inner diameter larger than the outer diameter of the light-blocking cylinder 9b such that the movement of the intermediate part 10 is not restricted by the light-blocking cylinder 9b when the intermediate part 10 moves in the horizontal direction with respect to the microscope attachment part 9.

Figure 5:
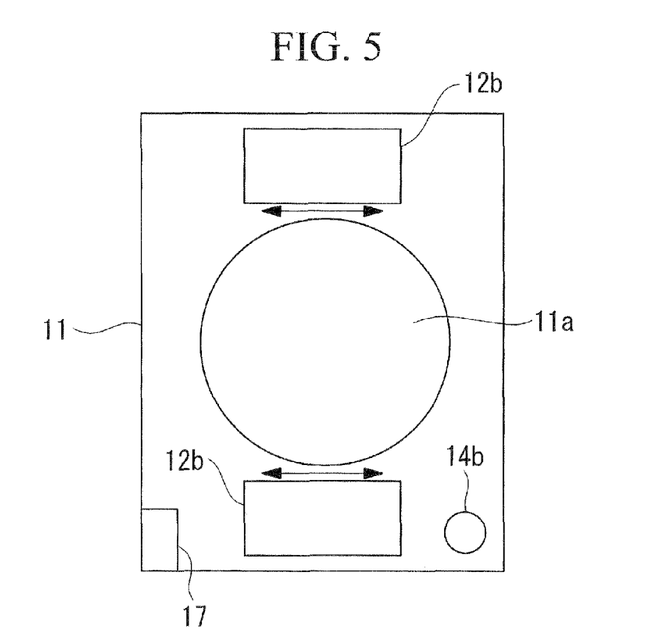
FIG. 5 is a front view of an objective attachment part of the positioning unit in FIG. 2.

As illustrated in FIG. 5, an objective attachment screw hole 11a, from which the rear section of the objective optical system 3 is removable, penetrates through substantially the center of the objective attachment part 11.

A microscope-side centering screw hole (optical-axis adjusting member) 14a and an objective-side centering hole (optical-axis adjusting member) 14b into which a centering screw (optical-axis adjusting member) 13 is inserted penetrate the microscope attachment part 9 and the objective attachment part 11, respectively, in the thickness direction thereof, at positions that align with the light-blocking cylinder 9b and the objective attachment screw hole 11a when they are disposed on substantially concentric axes. The centering screw 13 has a screw part 13a at the rear section and a cone part 13b, which is gradually tapered, at the tip section. The screw part 13a is engaged with the microscope-side centering screw hole 14a. The cone part 13b is inserted into the objective-side centering hole 14b.

In this way, when a turning screw 13c provided at an intermediate position of the centering screw 13 is turned in a tightening direction, the position of the objective attachment part 11 is adjusted to a position where the optical axis of the objective optical system 3 and the optical axis of the microscope 2 align. In addition, by providing notches 10b at the four corners of the intermediate part 10, the intermediate part 10 and the centering screw 13 are movable without their positions being restricted.

Furthermore, a securing screw hole (restricting member) 15b with which a securing screw (restricting member) 15a is engaged is formed in the microscope attachment part 9. By tightening the securing screw 15a, a shim 16 interposed between the securing screw 15a and the microscope attachment part 9 is secured to the microscope attachment part 9. In this way, the objective attachment part 11 is secured to the microscope attachment part 9 via a coupling member 17, which couples the shim 16 and the objective attachment part 11.

Figure 6:
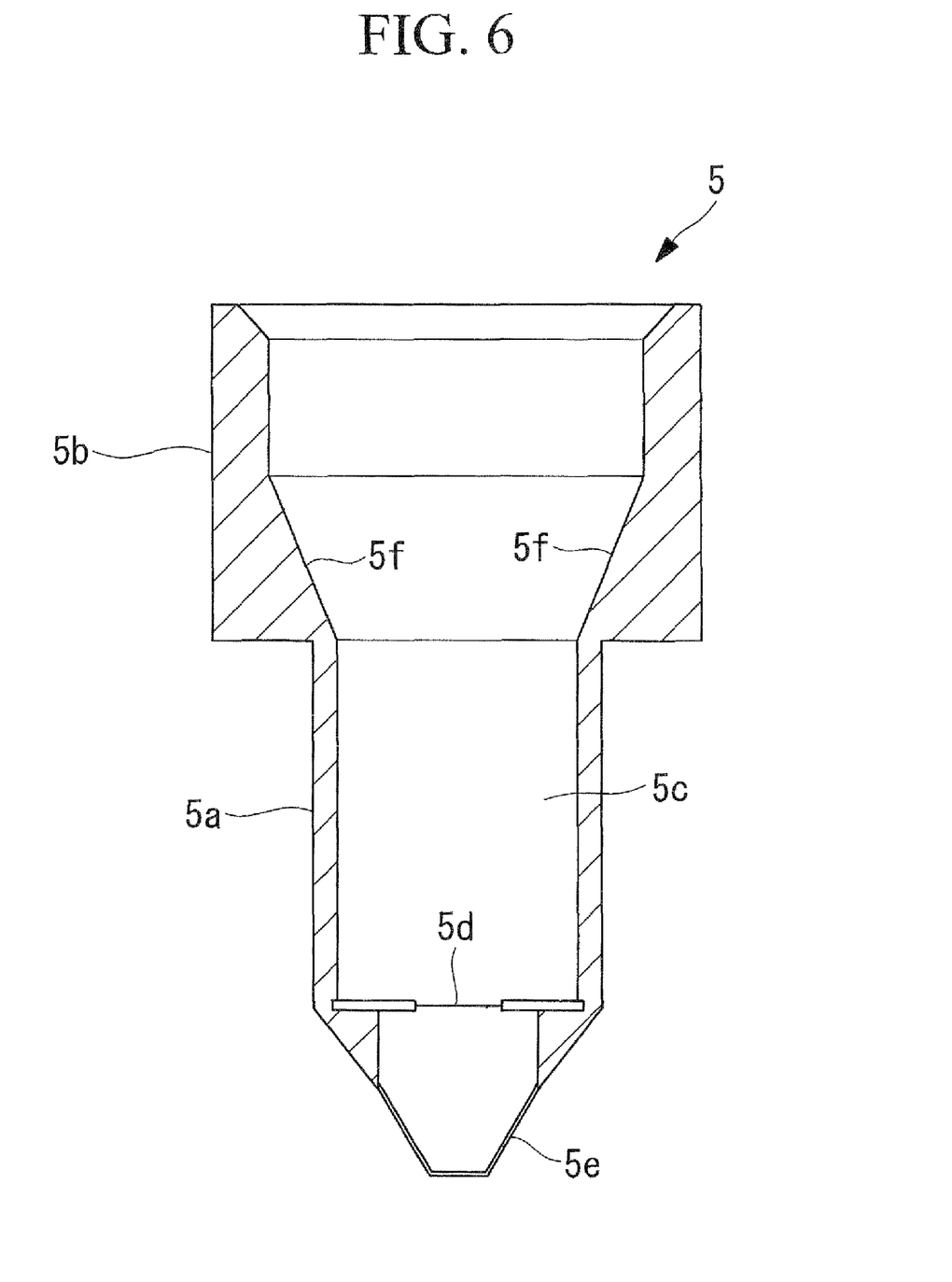
FIG. 6 is a sectional side view illustrating a support unit of the objective-optical-system positioning apparatus in FIG. 1.

The support unit 5 is substantially cylindrical, and, as illustrated in FIG. 6, has a small-diameter part 5a, which is inserted into the organism, and a large-diameter part 5b having a diameter larger than that of the small-diameter part 5a. Inside the small-diameter part 5a, an insertion hole 5c having an inner diameter that is slightly larger than the outer diameter of the small-diameter end section 3a of the objective optical system 3 extends in the longitudinal direction. At the bottom of the insertion hole 5c, a window 5d made of a transparent material, such as cover glass, is provided at the center section, which serves as a light path between the objective optical system 3 and the specimen surface.

The tip of the small-diameter part 5a is blocked with a transparent member 5e, such as glass, at a distance that creates an appropriate space between the bottom of the insertion hole 5c and the specimen surface. In this way, when the small-diameter end section 3a is inserted into the insertion hole 5c until the surface at its tip bumps into the bottom of the insertion hole 5c, the objective optical system 3 is appropriately focused at the specimen surface.

The large-diameter part 5b has an inner surface 5f, which is a cone-shape that continues, with an increasing diameter, from the inner surface of the insertion hole 5c.

Figure 7:
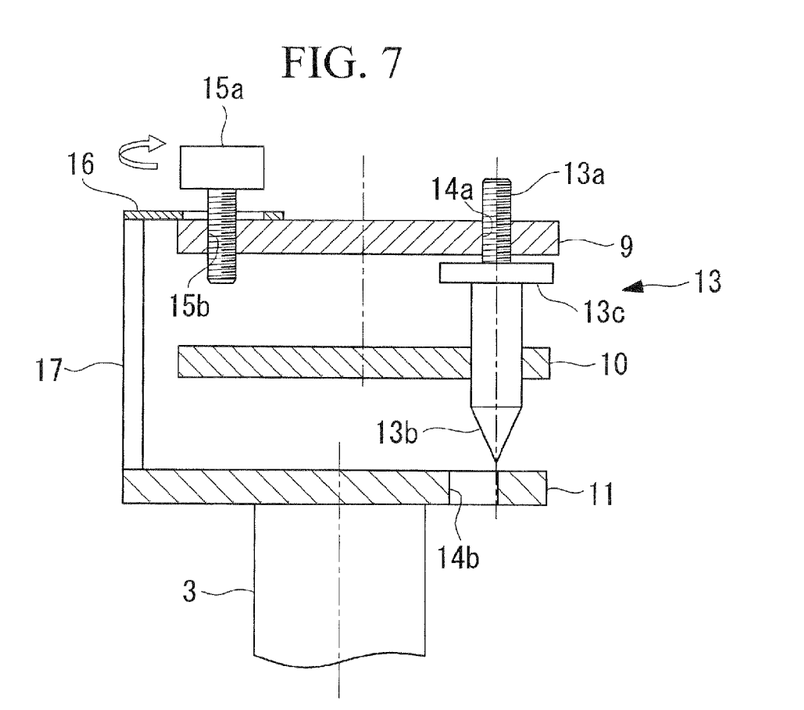
FIG. 7 is a diagram illustrating the usage of the objective-optical-system positioning apparatus in FIG. 1 and illustrates a state in which the objective optical system is freely moveable.
Figure 8:
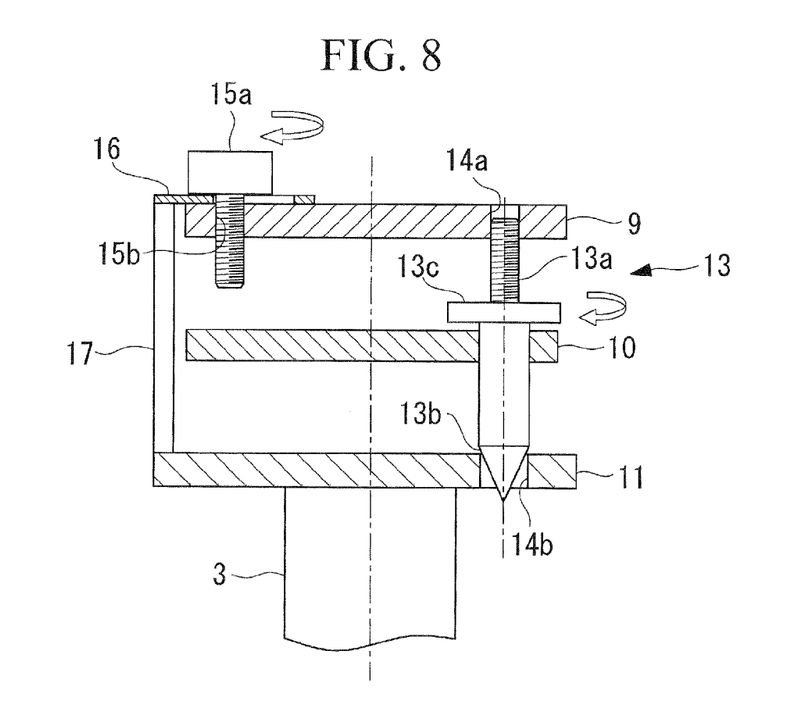
FIG. 8 is a diagram illustrating the usage of the objective-optical-system positioning apparatus in FIG. 1 and illustrates a state in which the optical axis of the objective optical system is being adjusted.
Figure 9:
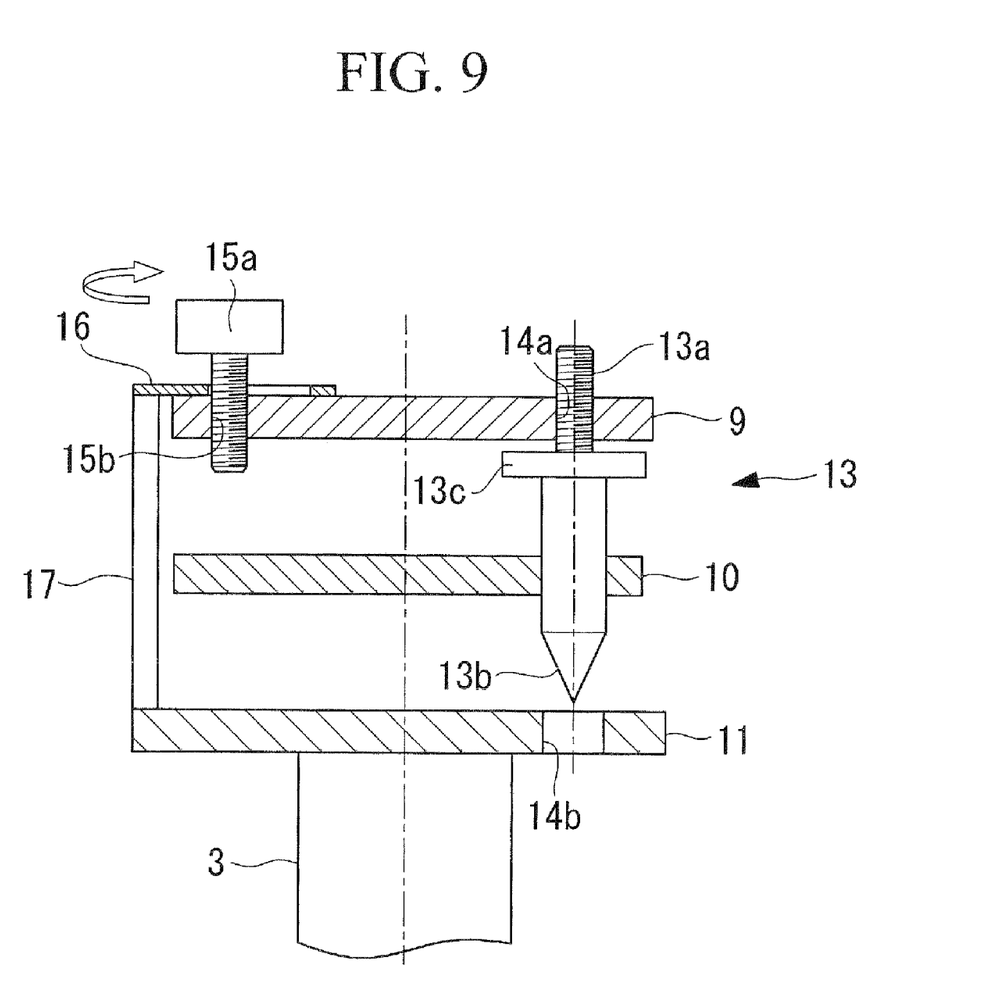
FIG. 9 is a diagram illustrating the usage of the objective-optical-system positioning apparatus in FIG. 1 and illustrates a state when a specimen is moved close to the objective optical system.

The use and operation of the objective-optical-system positioning apparatus 1 and the examination apparatus 100 having such configurations will be described below with reference to FIGS. 7 to 10. In FIGS. 7 to 9, parts of the configurations are omitted for the sake of simplifying the description of these configurations.

To carry out in vivo examination of the inside of the brain of the mouse A using the examination apparatus 100 according to this embodiment, the support unit 5 is secured by bonding, with the small-diameter part 5a inserted into a through-hole penetrating the skull of the mouse A, thereby securing the head of the mouse A to the stage 7.

First, by loosening the securing screw 15a, the objective optical system 3 is set to a state in which it is freely movable on a substantially horizontal surface (refer to FIG. 7). Next, the centering screw 13 is tightened to adjust the optical axis of the objective optical system 3 and the optical axis of the microscope 2 to aligned positions. Subsequently, the securing screw 15a is tightened to secure the objective optical system 3 to the microscope 2 (refer to FIG. 8), and, in this state, the centering screw 13 is loosened. At this time, the optical axis of the objective optical system 3 is held at a position aligned with the optical axis of the microscope 2.

Next, the stage 7 is moved such that an insertion hole 15c is disposed substantially vertically downward from the objective optical system 3 to align the objective optical system 3 and the examination site. Then, the securing screw 15a is loosened to set the objective optical system 3 to a freely movable state (refer to FIG. 9), and the objective optical system 3 is slowly moved downward to insert the small-diameter end section 3a into the insertion hole 5c.

Figure 10:
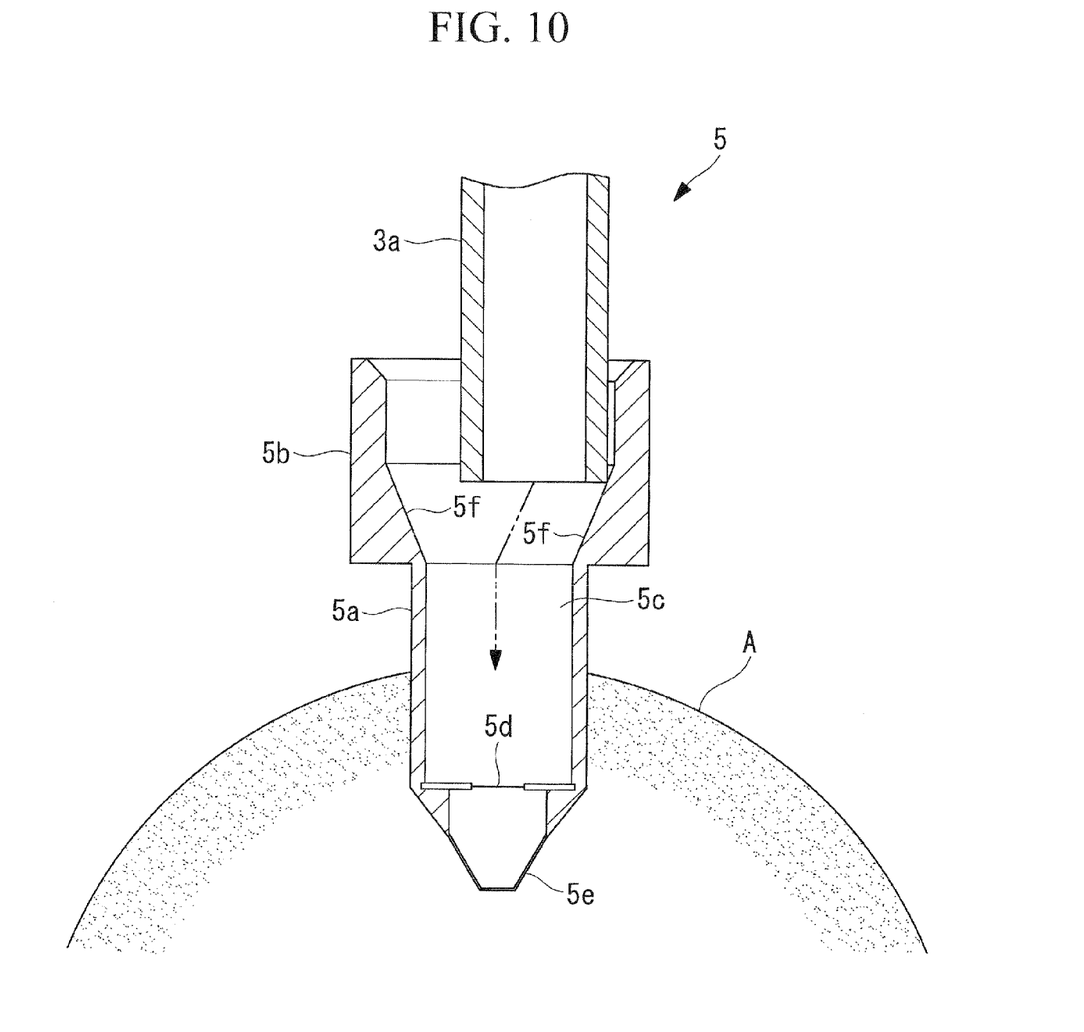
FIG. 10 is a diagram illustrating the process of inserting the objective optical system into an inserting hole using the objective-optical-system positioning apparatus in FIG. 1.

At this time, if the position of the objective optical system 3 is misaligned relative to the insertion hole 5c, the tip of the small-diameter end section 3a contacts the tapered inner surface 5f (refer to FIG. 10). Then, the tip of the small-diameter end section 3a smoothly moves along the inner surface 5f, is guided to the position of the insertion hole 5c, and is directly inserted into the insertion hole 5c. After the small-diameter end section 3a is inserted until it strikes the bottom of the insertion hole 5c, the securing screw 15a is tightened to fix the position of the objective optical system 3. Through the above-described process, the inside of the brain of the mouse A can be examined in vivo using the microscope 2.

In this way, according to this embodiment, the inner surface 5f, whose diameter gradually decreases toward the insertion hole 5c, is provided on the support unit 5. Furthermore, the objective optical system 3 is inserted into the insertion hole 5c while being smoothly and freely movable in a direction intersecting the insertion direction. In this way, the position of the small-diameter end section 3a is adjusted during the insertion process even when its position is misaligned. Therefore, there is an advantage in that, even when the inner diameter of the insertion hole 5c is decreased to substantially the same as the outer diameter of the small-diameter end section 3a, the small-diameter end section 3a can be easily inserted into the insertion hole 5c without requiring highly precise position control of the objective optical system 3.

Furthermore, there is an advantage in that, by decreasing the diameter of the insertion hole 5c as much as possible in this way, the inside of the body of the mouse A can be examined over a relatively long period of time while reducing the invasiveness the support unit 5 on the mouse A. Moreover, even when the tip of the small-diameter end section 3a contacts the tapered inner surface 5f, the small-diameter end section 3a smoothly moves in a direction that absorbs the impact due to the contact. In this way, there is an advantage in that damage to the small-diameter end section 3a and the support unit 5 can be prevented, and, furthermore, any influence on the organism or examination site due to the impact at contact can be prevented.

Furthermore, even when the configuration of the objective optical system 3 is such that it is freely movable in a direction intersecting the optical axis, the position of the objective optical system 3 is fixed relative to the microscope 2 when required through a simple method. In this way, there is an advantage in that it is possible to prevent inconveniences such as the optical axis being misaligned due to the objective optical system 3 moving after adjusting the optical axis, and furthermore, a more stable image can be acquired by preventing blurriness of the field of view during examination.

In the above-described embodiment, the unit attachment part 6 is movable in the direction of the optical axis of the objective optical system 3. Instead, however, the stage 7 may be movable in the direction of the optical axis of the objective optical system 3.

Even in this way, the same advantages as those according to the above-described embodiment can be achieved.

Moreover, in the above-described embodiment, the upright microscope 2 is used. Instead, however, an inverted microscope may be used.

Furthermore, in the above-described embodiment, the microscope attachment part 9 is attached to the microscope 2 by the microscope attachment screw 9a with a structure that is the same as that of the mount of the objective optical system 3. Instead, however, the microscope 2 may be attached by a structure that is the same as that of a revolver mount.

Furthermore, in the above-described embodiment, instead of the objective optical system 3, a revolver may be attached to the objective attachment part 11. By doing so, a plurality of objective optical systems 3 each having a different specification may be attached to the revolver, which is attached to the objective attachment part 11, and examination can be performed while easily changing the magnification, etc.

Furthermore, in the above-described embodiment, the angle between the objective optical system 3 and the stage 7 may be adjustable. In this case, the stage 7 may be tilted, and the optical system including the objective optical system 3 and the positioning unit 4 may be tilted.

It is also possible to dispose the support unit 5 secured to the head of the mouse A such that the longitudinal direction of the insertion hole 5c is tilted with respect to the optical axis of the objective optical system 3. Accordingly, by adjusting the angle between the stage 7 and the objective optical system 3 such that the longitudinal direction of the insertion hole 5c is aligned with the direction of the optical axis of the objective optical system 3, the small-diameter end section 3a can be easily inserted into the insertion hole 5c from an appropriate direction.

At this time, for example, in a state in which the specimen is secured to the stage 7, a rod-like member having a length approximately the same as that of the objective optical system 3 or an object having the same shape as that of the outer cylinder of the objective optical system 3 may be inserted into the insertion hole 5c, and the angle between the stage 7 and the objective optical system 3 may be adjusted such that the center axes thereof are aligned with the optical axis of the microscope 2. In this way, the angle between the stage 7 and the objective optical system 3 can be easily adjusted. Instead, a reflective member, e.g., mirror, which reflects light, may be attached at a position where the insertion hole 5c is covered. In such a case, selecting an angle that maximizes the intensity of an image examined by the microscope 2, the angle between the stage 7 and the objective optical system 3 can be easily adjusted.

What is claimed is:

1. An objective-optical-system positioning apparatus comprising:
a positioning unit interposed between an objective optical system having a small-diameter end section and an examination optical system configured to examine light collected by the objective optical system; and
a substantially cylindrical support unit, one end of which is secured to an organism, and which internally supports the small-diameter end section in a detachable manner,
wherein the positioning unit includes a holding part for holding the objective optical system and a moving mechanism supporting the holding part, the moving mechanism including two linear guides which guide the holding part such that the holding part is freely movable in directions orthogonal to each other on a plane substantially orthogonal to a direction of an optical axis of the objective optical system, and wherein the support unit has a tapered inner surface whose diameter gradually increases toward the other end which is not secured to the organism.

2. The objective-optical-system positioning apparatus according to claim 1, wherein the linear guides have bearing mechanisms.

3. An examination apparatus comprising:
the objective-optical-system positioning apparatus according to claim 2.

4. The objective-optical-system positioning apparatus according to claim 1, further comprising:
a restricting member configured to restrict movement of the holding part.

5. An examination apparatus comprising:
the objective-optical-system positioning apparatus according to claim 4.

6. The objective-optical-system positioning apparatus according to claim 1, further comprising:
an optical-axis adjusting member configured to adjust a position of the optical axis of the objective optical system held by the holding part such that the position of the optical axis of the objective optical system is aligned with a position of an optical axis of the examination optical system.

7. An examination apparatus comprising:
the objective-optical-system positioning apparatus according to claim 6.

8. An examination apparatus comprising:
the objective-optical-system positioning apparatus according to claim 1.

* * * * *